United States Patent [19]

Diepers

[11] 4,437,033
[45] Mar. 13, 1984

[54] ULTRASONIC TRANSDUCER MATRIX HAVING FILLER MATERIAL WITH DIFFERENT ACOUSTICAL IMPEDANCE

[75] Inventor: Heinrich Diepers, Höchstadt, Fed. Rep. of Germany

[73] Assignee: Siemens Aktiengesellschaft, Munich, Fed. Rep. of Germany

[21] Appl. No.: 267,583

[22] Filed: May 27, 1981

[30] Foreign Application Priority Data

Jun. 6, 1980 [DE] Fed. Rep. of Germany ......... 302144

[51] Int. Cl.³ .......................................... H01R 17/06
[52] U.S. Cl. ..................... 310/334; 73/626; 310/337; 367/155
[58] Field of Search ............... 73/596, 597, 603, 625, 73/626, 628; 367/153, 155, 170; 310/322, 334, 310/337

[56] References Cited

U.S. PATENT DOCUMENTS

| 4,281,550 | 8/1981 | Erikson | 73/626 |
| 4,324,142 | 4/1982 | Auphan et al. | 73/626 |
| 4,371,805 | 2/1983 | Diepers et al. | 310/334 |

OTHER PUBLICATIONS

German Patent 2,829,570 (U.S. patent application Ser. No. 49,898) —"Ultrasonic Head".

Primary Examiner—J. D. Miller
Assistant Examiner—D. L. Rebsch
Attorney, Agent, or Firm—Kenyon & Kenyon

[57] ABSTRACT

An ultrasonic transducer arrangement having a matrix of oscillators, each such ultrasonic oscillator being formed of a matrix of columnar transducer elements which are electrically controlled together. The spaces between the individual transducer elements are filled with a filler material having an acoustic impedance which substantially differs from the acoustic impedance of the ultrasonic oscillator material from which the transducer elements are formed. The ultrasonic oscillators are provided with electrode strips which are arranged in parallel rows on one flat side of the matrix. The other side of the matrix is provided with electrode strips in the form of parallel columns, so as to be transverse to the direction of the electrode strips on the first side. This arrangement permits high-packing density of the transducer elements, resulting in high resolution which enables line focusing and a close approximation of point focusing.

3 Claims, 5 Drawing Figures

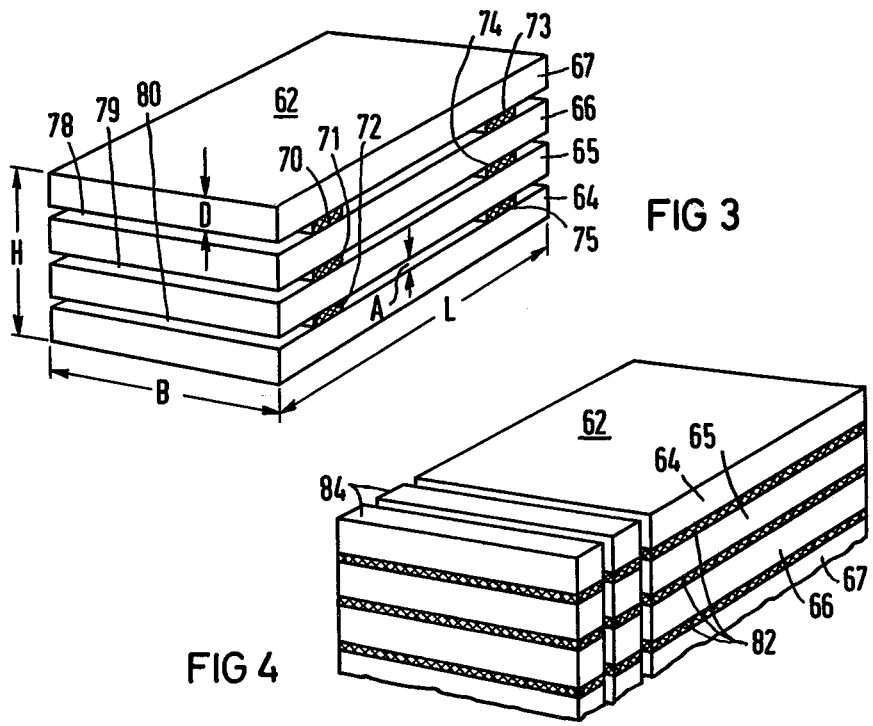
FIG 3
FIG 4
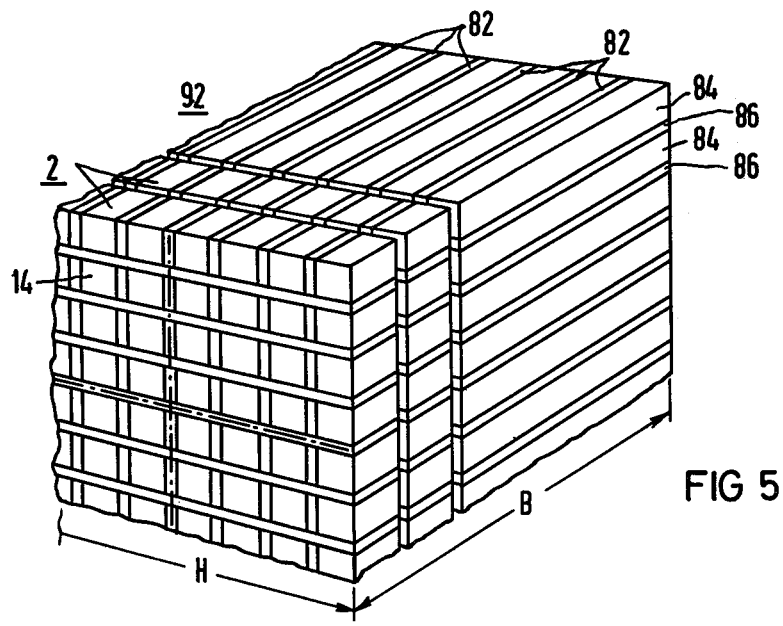
FIG 5

ULTRASONIC TRANSDUCER MATRIX HAVING FILLER MATERIAL WITH DIFFERENT ACOUSTICAL IMPEDANCE

BACKGROUND OF THE INVENTION

This invention relates generally to ultrasonic transducers, and more particularly, to an ultrasonic transducer arrangement having a matrix of ultrasonic oscillators.

Ultrasonic arrays, illustratively of the type used in medical diagnostic equipment, are configured from a relatively large oscillator slab which is then electrically or mechanically subdivided to produce groups of individual oscillators, which may be arranged in a linear configuration. Electrical subdivision is achieved by applying separate electric contact areas, generally in the form of a surface metallization, in regularly arranged rectangular zones. Once the oscillator groups have been formed, the oscillator material is polarized by the electric contact areas, which are provided with electric leads. The transducer elements are then arranged between a damper body and a matching body.

One known transducer comb for an ultrasonic transducer array is known as the compound scanner type, and is formed of a linear arrangement of ultrasonic oscillators. The ultrasonic oscillators can be subdivided into acoustically and mechanically separated transducer elements, by fine subdivision techniques, the separated transducer elements being connected electrically in parallel in groups which are controlled simultaneously. It is generally desirable to keep the width of the transducer elements substantially less than one half of the wave length ($\lambda/2$) of the radiated or received ultrasound waves. German Pat. No. 28 29 570 teaches a matrix of transducer elements of the type described hereinabove having additional transverse gaps.

In ultrasonic transducer arrangements of the type which are finely subdivided by mechanical operations, the spacing between the transducer elements, which is determined by the width of the mechanical cut, cannot be made arbitrarily small. As the width of the transducer elements themselves is decreased, the losses which result from the subdivision operation increase because the size of the spaces between the transducer elements approaches the size of the transducer elements themselves. Such losses are further increased if a matrix of transducer elements is produced with additional transverse subdivision. As a result of their mechanical separation, the transducer elements do not produce a form-locking structural unit, and therefore, electrical contacts are expensive to apply to arrangements having many transducer elements.

It is, therefore, an object of this invention to provide a matrix of ultrasonic oscillators which have a large number of transducer elements having very small widths and small spacing therebetween, which forms a mechanically strong structural unit and which can be contacted and controlled in a simple manner so as to permit electronic focusing and variable aperture.

Ultrasonic arrays used in mechanical diagnostics are provided with B-displays for preparing sectional images. Such ultrasonic arrays are provided with a mechanical focus arrangement in the longitudinal direction of the ultrasonic array, and an electronic focus in the direction perpendicular to the longitudinal. The electronic focus can be moved in depth (i.e., parallel to the direction of radiation) by controlling the excitation of the oscillators in a group. Such focusing, however, cannot be achieved with a mechanical focusing arrangement which may be formed, for example, by a cylindrical curvature of the radiating surface. A substantial technological effort would be required to achieve the advantages of electronic focusing in the direction where only mechanical focusing is available.

SUMMARY OF THE INVENTION

The foregoing and other objects are achieved by this invention which solves the above-mentioned problems by providing an ultrasonic transducer arrangement having a matrix of ultrasonic oscillators, the ultrasonic oscillators consisting of a matrix of columnar transducer elements which are electrically controlled together, and which have a height which exceeds their thickness. The spaces between the ultrasonic oscillators and the spaces between the individual transducer elements are filled with a filler substance having an acoustic impedance which is substantially different from the acoustic impedance of the oscillator material, and which provides a form-locking mechanical connection between the transducer elements. The electrodes of the transducer elements are provided in rows on one flat side of the matrix, and in columns on the other flat side.

Electronic focusing is achieved by controlling the rows and columns of conductive material on the flat sides of the matrix with signals which are delayed with respect to one another. Moreover, a variable aperature may be obtained by either connecting or disconnecting, in steps, the columns and rows on the outer ends of the oscillator groups. The strong mechanical structure of the matrix which is formed of a multiplicity of ultrasonic oscillators, each such ultrasonic oscillator being formed of a plurality of a transducer elements, permits high packing density to be achieved, with a correspondingly large radiating surface. In one embodiment, the spacings between the transducer elements may be in the order of a few microns, illustratively 5 microns, thereby enabling high sensivity. The inventive technique for producing the contacts, and the electronic control, permit a line focus and, at least approximately, a point focus to be obtained.

The matrix consists of column-like transducer elements which have a thickness, perpendicular to the flat sides of the matrix, which is at least twice the width of the transducer elements in a direction parallel to the flat sides of the matrix.

The matrix of transducer elements can be fabricated in a simple manner by stacking plates of ultrasonic oscillator material, with their flat sides stacked on top of each other, the plates being alternated with thin intermediate layers of the filler material to produce a mechanically strong bond between the filler material and the plates. Several plate-shaped bodies are made by producing respective cuts, perpendicular to the plane of the stack and parallel to the width, and one behind the other in the direction of the length of the stack. These bodies are then stacked with their flat sides on top of each other alternately with a thin intermediate layer of filler material and a mechanically strong bond between the filler material and the formed bodies. The matrix containing the transducer element is produced by a cut perpendicular to the stacking plane of the formed bodies. Each group of transducer elements which is to form an ultrasonic oscillator is provided at its end faces which lie in one of the flat sides of the matrix, with a metallization which serves as the current lead. Rows and columns are formed on the flat sides of the matrix, the rows and columns being connected to an electric control conductor via corresponding electrical connections.

BRIEF DESCRIPTIONS OF THE DRAWINGS

Comprehension of the invention is facilitated by reading the following detailed description in conjunction with the annexed drawings, in which:

FIGS. 3 to 5 illustrate the sequence of steps which are used in the manufacture of the ultrasonic transducer arrangement.

DETAILED DESCRIPTION

Figure 1:
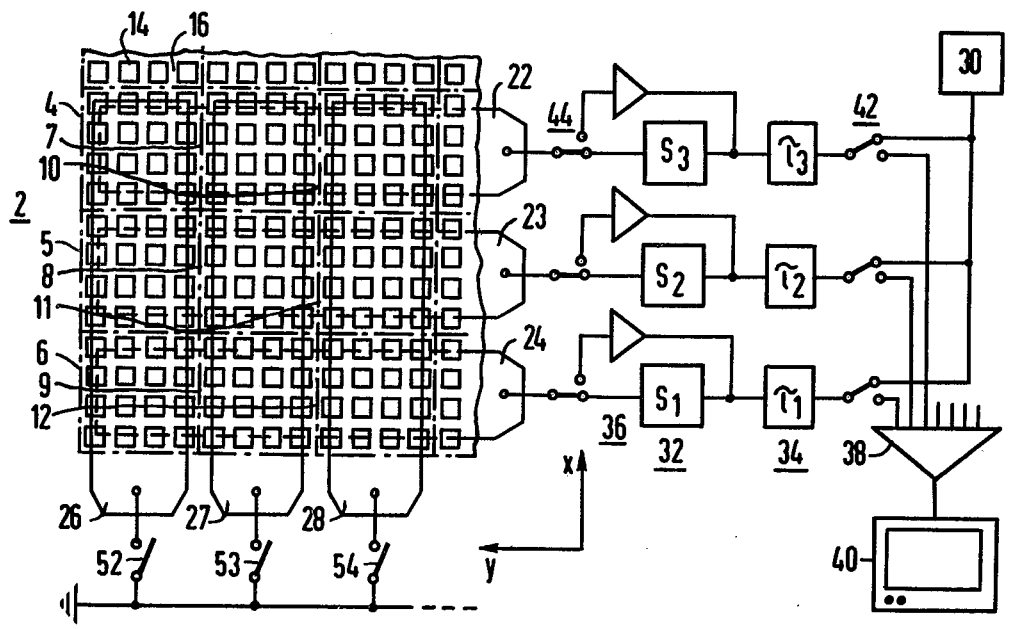
FIG. 1 is an illustration of a top view of an ultrasonic transducer arrangement according to the invention having circuitry for electrically controlling the transducer elements.

FIG. 1 shows a matrix 2 of ultrasonic oscillators of which only ultrasonic oscillators 4 through 12 are shown in the figure. Each of ultrasonic oscillators 4 through 12 is provided with a frame which is represented by a dash-dotted line. The ultrasonic oscillators consist of a matrix of columnar transducer elements 14 which are provided at their end faces on a flat side of the matrix 2 with common electric contacts (not shown in this figure). Such common electric contacts permit transducer elements 14 in the column to be electrically controlled together. In order to preserve the clarity of the drawing, spaces 16 between transducer elements 14 are shown enlarged, and therefore not in proportion. Ultrasonic oscillators 4, 7, and 10; 5, 8, and 11; and 6, 9, and 12 are arranged in respective rows 22, 23, and 24 by respective common electrical connections which are indicated by dashed lines around the common electric contacts. On the upper flat side of matrix 2, ultrasonic oscillators 4, 5, and 6; 7, 8, and 9; and 10, 11, and 12, form columns 26, 27, and 28, respectively, by common electric contacts. Rows 22, 33, and 24 are associated with an ultrasonic transmitter having a common clock 30 for generating timing signals, and respective transmitters $S_1$, $S_2$, and $S_3$, of transmitter chain 32. Transmitters $S_1$, $S_2$, and $S_3$ receive clock pulses via respective double-throw switches 42, which may be of the electronic type, and an electronic delay stage 34 having individual delay stages $\tau_1$, $\tau_2$, and $\tau_3$. Delay chain 34 is associated with the transmitter, as well as with a receiver which contains an electronic amplifier chain 36, a summing amplifier 38, and a screen 40. Transmitter pulses are conducted to ultrasonic oscillators 4 through 12 by respective double-throw switches of an electronic switch 44. The echo pulses are conducted via a respective switch in electronic switch 44, an amplifier stage of amplifier chain 36, a respective one of delayed stages 34, and the associated one of double-throw switches 42, to summing amplifier 38 so as to provide a visual readout on picture screen 40. In preferred embodiments of the invention, electronic switches 42 and 44 may be incorporated in integrated circuitry. Particularly with respect to electronic switch 44, the insertion loss of each switch in the open state should be at least 40 dB.

Electronic switches 52, 53, and 54 are assigned to respective columns 26, 27, and 28. The common contact arrangement of rows 22, 23, and 24, and columns 26, 27, and 28, each consist of a metallization in the form of a strip, which may consist, illustratively, of a metal layer of gold-platinum-gold sputtered thereon. The width of these strips covers all of the transducer elements in the jointly controlled ultrasonic oscillator which are to oscillate in phase. In one embodiment, the width of each strip is approximately 3 millimeters, in an ultrasonic array which operates at approximately 2.5 megahertz. Several rows of ultrasonic oscillators, which are electrically connected to one another to form a group, comprise the beam aperature. The electronic stepping of this group along the ultrasonic array in the X-direction produces the picture on screen, in a line by line format. Columns 26, 27, and 28, which are on the upper flat side of matrix 2, are connected by switches 52, 53, and 54, respectively, to a common potential, which in this embodiment corresponds to a zero potential.

Figure 2:
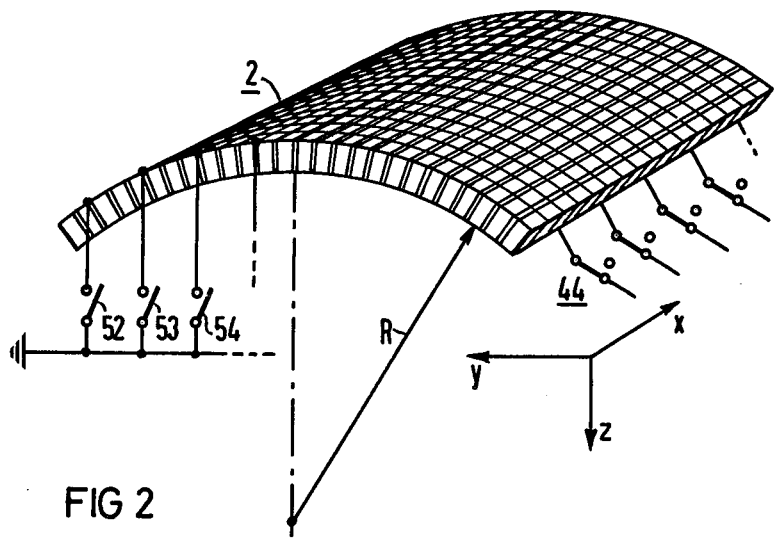
FIG. 2 is a perspective view of an ultrasonic transducer arrangement having mechanical focusing.

FIG. 2 shows matrix 2 which is bent about its longitudinal axis to produce a mechanical focus in the Y-Z plane. Such a curvature may be achieved by conforming the array to shaped bodies before the filler material 16 is fully hardened. It may be advantageous to bend matrix 2 at an elevated temperature of approximately 40° C. After such bending, the hardening of the shaped bodies is completed under the conditions specified by the manufacturer of the filler material 16. The electronic focusing is achieved in the X-Z plane by appropriately delaying the addressing of the rows which are connected via double-throw switches 44. A radius R of the curvature of matrix 2 determines the depth of the focal point within the body (not shown) to be examined.

The curvature of matrix 2 with radius R need not be limited to cylindrical configurations. Such curvature may be parabolic, hyperbolic, or in the form of a roof shape (Axicon array). The different curvatures enable the production of focal zones having different widths and lengths. In addition, the position of the focus can be further optimized by the above-described selectable aperature, especially in situations wherein it is desired to narrow the sound beam beyond the natural focus at a predetermined depth. As in the case of the plane arrangement of the matrix of FIG. 1, electronic focusing in the X-Z plane may be achieved by utilizing delay stages $\tau_1$, $\tau_2$, and $\tau_3$ of delayed chain 34 in FIG. 2, to insert a propagation time delay. A dynamic focus is achieved by changing the delay times in accordance with the propagation velocity of the ultrasonic pulse.

The duration of the delay is selected so that the focus is placed at a depth, within the body to be examined, from which the pulse reply is expected. The depth of the natural focus in the Y-Z plane depends upon the size of the aperature and the wave length of the ultrasonic energy in the body under test. Advantageously controlling columns 26, 27, and 28 so as to change the aperature permits the natural focus to be placed in the vicinity of the electronic focus of rows 22, 23, and 24. To this end, the columns situated at the beginning and end of matrix 2 in the X-direction are electrically separated from matrix 2 by opening switches 52, 53, and 54. Thus, a focus which approximates a point is obtained. In some circumstances, it may be advantageous to connect or disconnect several adjacent columns at the beginning and end of the matrix in the Y-direction simultaneously.

FIG. 3 shows the initial steps for manufacturing matrix 2 with transducer elements 14, shown in FIG. 1. A large number of strip-shaped plates 64 through 67 are made, as shown in FIG. 3, from ultrasonic oscillator material, which may be formed from the cutting of a piezo-ceramic block, and assembled into a stack. Plates 64 through 67 may consist, for instance, of lead, zirconate, titanate Pb(ZrTi)O$_3$ or lead metaniobate Pb(NbO$_3$)$_2$, or of another oscillator material. The thickness of plates 64 through 67 may be in the order of 100 microns, or less. Spacers 70 through 75 are arranged between plates 64 through 67, the spacers being formed of strips of a plastic film, the thickness of which is determined by the spacing A of the plates, spacing A being substantially smaller than thickness D of the plates 64 to 67. The number of plates, of which only four are shown in the figure for simplification, is chosen to be equal to the desired number of transducer elements which are to be arranged in a row in the matrix. In some embodiments, such a number may in the order of several hundred. Plates 64 to 67 of stack 62 are secured, illustratively by a clamp (not shown), and gaps 78 to 80, between plates 64 to 67, are filled with a filler material which has an acoustic impedance which is substantially different from that of the ultrasonic oscillator material of plates 64 through 67. Thus, the acoustic impedance of the filler material may be substantially smaller or substantially larger than that of the plate material, which may be a function of the density of the ultrasonic oscillator material and the velocity of propagation of the vibration mode in question. The filler material may consist of a self-hardening plastic, preferably Araldit, and epoxy resin, or a silicone rubber. Gaps 78 to 80 can be filled with the filler material by pouring, or by immersion of stack 62.

FIG. 4 shows a shaped body 84 which is produced after the filler material 82 between plates 64 to 68 has hardened. The shaped body may be formed by cutting slabs in a direction perpendicular to the stack plane, and parallel to the directions of width B and length L of stack 62. The thickness of formed bodies 84 determines the thickness of the transducer elements in matrix 2.

The formed bodies 84, which contain in their longitudinal direction strips of piezoelectric material alternating with intermediate layers of filling material, are stacked in large numbers in the manner shown in FIG. 3. First, spacers are arranged between the formed bodies 84, and the gaps which are produced are filled with a filler material which may be a self-hardening plastic material.

In accordance with a different aspect of the invention, formed bodies 84 can be provided, at least on one of their flat sides, with a thin superficial layer of filler material 86, which is shown in FIG. 5. Filler material 86 can be sprayed-on, sputtered-on, or printed-on. Filler material 86 establishes a strong adhesion bond between plates 84. Alternatively, the flat sides of shaped bodies 84 may be coated with filler material and cemented to one another. After filler material 86 has set, a matrix 2 of transducer element 14 is produced by a cut parallel to the longitudinal direction H. Several such matrices 2 are stacked along direction B behind one another. Within each matrix 2, adjacent transducer elements 14 are provided at their end faces with common electrical contacts, so as form ultrasonic oscillators in the manner indicated by the dash-dotted dividing line in FIG. 5. The distance between cuts within stack 92 determines the length of the columnar transducer elements 14, and is preferably selected as large as the thickness D of plates 64 to 67, which simultaneously determines the width of transducer elements 14.

The oscillator material can be electrically polarized before slabs 64 through 67 are cut from a block of the oscillator material. The sectional planes are then selected during subsequent process steps so that transducer elements 14 are polarized perpendicularly to the flat sides of matrix 2. However, such electric polarization may also occur when matrix 2 in FIG. 5 is completed and the transducer elements are provided with electrical contacts.

Although the invention described herein has been disclosed in terms of specific embodiments and applications, other embodiments, in light of this teaching, would be obvious to persons skilled in the art. Accordingly, it is to be understood that the drawings and descriptions are illustrative of the principles of the invention, and should not be construed to limit the scope thereof.

What is claimed is:

1. An ultrasonic transducer arrangement having a matrix of ultrasonic oscillators, the arrangement further comprising:

a plurality of ultrasonic oscillators, each ultrasonic oscillator consisting of a matrix of columnar transducer elements which are electrically controlled simultaneously, each transducer element having a uniform thickness throughout its height, the height of each such element being substantially greater than the thickness thereof;

filler material interposed between individual ones of the transducer oscillators, and between individual ones of the transducer elements, said filler material being limited in extent to the height of the transducer elements and having an acoustic impedance which is substantially different from the acoustic impedance of the oscillator material of the transducer elements, and for providing a structurally locking connection between adjacent ones of the transducer elements throughout their height;

a plurality of electrode conductor strips disposed on either side of said matrix of columnar transducer elements, said electrode conductor strips being arranged parallel to one another so as to form rows of electrode conductor strips on one side of said matrix, and parallel to one another on the other side of said matrix in a direction transverse to said rows of electrode conductor strips to form columns of electrode conductor strips on said other side of said matrix; and a plurality of electronic delay stages associated with respective ones of said rows of electrode conductor strips, said columns of electrode conductor strips and said rows of electrode conductor strips being separately controllable.

2. The ultrasonic transducer arrangement of claim 1 wherein said columns and rows of said electrode conductor strips of the matrix are controllable in respective groups of neighboring ones of said transducer elements.

3. The ultrasonic transducer arrangement of claim 1 wherein the matrix of ultrasonic oscillators is provided with a curvature whereby said rows of electrode conductor strips are curved.

* * * * *